United States Patent [19]

Demny et al.

[11] 4,061,542

[45] Dec. 6, 1977

[54] 2-METHYL-L-ARGININE PRODUCED BY CULTIVATING STREPTOMYCES STRAIN

[75] Inventors: Thomas Casimir Demny, Livingston; Hubert Maehr, Belleville, both of N.J.

[73] Assignee: Hoffmann-La Roche Inc., Nutley, N.J.

[21] Appl. No.: 664,834

[22] Filed: Mar. 8, 1976

[51] Int. Cl.$^2$ ............................................... C12D 9/14
[52] U.S. Cl. .................................... 195/80 R; 195/29; 260/534 R; 260/438.1; 548/313
[58] Field of Search ...................................... 195/80 R

[56] References Cited

U.S. PATENT DOCUMENTS

| 3,865,694 | 2/1975 | Berger et al. | 195/80 R |
| 3,993,545 | 11/1976 | Pruess et al. | 195/80 R |

Primary Examiner—Alvin E. Tanenholtz
Attorney, Agent, or Firm—Samuel L. Welt; Bernard S. Leon; William H. Epstein

[57] ABSTRACT

The compound 2-methyl-L-arginine having useful antibiotic and anti-bacterial properties and its methods of preparation from a new species of Streptomyces sp. X-11837 or from 5-hydroxy-2-pentanone.

2 Claims, No Drawings

2-METHYL-L-ARGININE PRODUCED BY CULTIVATING STREPTOMYCES STRAIN

SUMMARY OF THE INVENTION

In accordance with this invention, it has been discovered that 2-methyl-L-arginine which has the structure:

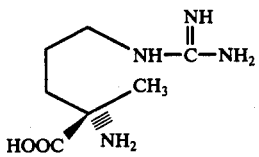

has useful antibiotic and antibacterial properties against such bacteria as *Escherichia coli B* and Bacillus.

In accordance with this invention, the compound of formula I can be produced from 5-hydroxy-2-pentanone which has the formula:

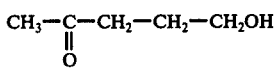

or by fermentation of Streptomyces sp. X-11837.

DETAILED DESCRIPTION OF THE INVENTION

The compound of formula I and its pharmaceutically acceptable salts, in accordance with this invention, have been found to be active against bacteria such as *Escherichia coli B* and Bacillus s.p. and to be useful as an antibiotic against bacteria such as *Escherichia coli B* and Bacillus s.p..

The anti-microbial properties of the compound of the formula I and its salts are shown by the paper-disc agar-diffusion assay as described by Scannell et al. *J. Antibiotics* 25: 179–184 (1972). In this assay, *Escherichia coli B* as test organism, the minimal agar medium described by Scanell et al. was employed for the initial detection and during isolation of the antimetabolite. Similar to $N^5$-hydroxy-L-arginine, the diameter of the inhibition zone was proportional to the logarithm of concentration of the compound of formula I within the range of 2 to about 100 µg/ml. A two-fold increase of the concentration of the compound of formula I increased the inhibition zone diameter by 3 mm and a 40 g/ml solution gave a zone of about 36 mm.

The compound of formula I showed approximately the same level of activity against *Bacillus sp.* (ATCC 27860) as againt *E. coli*. The antibiotic activity of the compound of formula I against *Escherichia coli* was reversed by L-arginine, L-citrulline, L-ornithine and $N^2$-acetyl-L-ornithine but not by L-glutamic acid.

The compound of formula I is relatively non-toxic to vertebrates. This can be seen from the fact that the dihydrate of the indanedione salt of the compound of formula I has a $LD_{50}$ of greater than 1 gm/kg when administered to mice by both i.p. and p.o. methods.

As indicated above, the compounds of formula I and its salt have the property of adversely affecting the growth of certain bacteria. It is useful in wash solutions for sanitary purposes as in the washing of hands and the cleaning of equipment, floor or furnishings or contaminated rooms or laboratories. The compound of formula I is also useful for suppressing the growth of sensitive organisms in plate assays and in microbiological mediums.

The compound L-2-methyl ornithine, produced by conventional basic hydrolysis of the compound of formula I, is, like D,L-2-methyl ornithine, an inhibitor of ornithine decarboxylase, an enzyme system which catalyzes the decarboxylation of putrescin (putrescin being utilized to produce spermidine). Thus 2-methyl-L-ornithine suppresses spermidine production and like D,L-2-methyl ornithine acts an an anti-fertility agent when administered to males.

The compound of formula I is prepared by cultivating a strain of Streptomyces species X-11837 in an aqueous carbohydrate solution containing a nitrogeneous nutrient under submerged aerobic conditions until substantial activity *Escherichia coli* and Bacillus bacteria is imparted to said solution and then recovering said compound of formula I from the solution.

The species Streptomyces X-11837 described herein includes all strains of Streptomyces which form a compound of formula I and which cannot be definitely differentiated from the culture number X-11837 and its sub-cultures including mutants and variants. The compound of formula I is identified herein and after this identification is known, it is easy to differentiate the strains producing a compound of formula I from others.

The organism producing the antibiotic of the present invention was isolated from a sample of soil collected in Port Harcourt, Nigera and is a new species designated Streptomyces species X-11837. A culture of the living organism, given the laboratory designation X-11837 has been deposited in the Northern Regional Research Labs (NRRL), Peoria, Ill. and added to its permanent collection of microorganisms (NRRL 8142 ).

Streptomyces X-11837 which is isolated from farmyard soil collected in Port Harcourt, Nigeria, grows on agar media with aerial hyphae and well developed branched mycelium penetrating into the agar. The submerged mycelium do not fragment, whereas some of the aerial hyphae differentiaed into spore chains. The chains are spiral with more than 10 spores per chain, the spores are spiny with average measurements of 0.9 to 1.0 by 1.3 to 1.7 µm. Chromatographic analysis of whole-cell hydrolyzate revealed the presence of diaminopimelic acid different from the meso-form.

The representative strain of Streptomyces sp. 11837 has been characterized as follows:

The formulation of the medium used in the description of the growth characteristics is classified below:

Medium 1 — Yeast extract — malt extract agar:

Bacto Yeast Extract (Difco) — 4.0 g.
Bacto-Malt Extract (Difco) — 10.0 g.
Bacto-Dextrose (Difco) — 4.0 g.
Distilled water — 1.0 liter
Adjust to pH 7.3. then add
Bacto-Agar — 20.0 g.
Liquify agar by steaming at 100° C. for 15–20 minutes Medium 2 — Oatmeal agar:

Oatmeal — 20 g.
Agar — 18.0 g.
Cook or steam 20 g. oatmeal in 1000 ml. distilled water for 20 minutes.
Filter through cheese cloth.
Add distilled water to restore volume of filtrate to 1000 ml.

Add trace salts solution — 1.0 ml. solution of 0.1 g. of each of $FeSO_4.7H_2O$, $MnCl_2.4H_2O$ and $ZnSO_4.7H_2O$ in 100 ml. distilled water.
Adjust to pH 7.2. with NaOH.
Add 18 g. agar; liquify by steaming at 100° C. for 15–20 minutes.

Medium 3 — Inorganic salts — starch agar:

Solution I: Difco soluble starch 10.0 g. Make a paste of the starch with a small amount of cold distilled water and bring to a volume of 500 ml.

Solution II:

$K_2HPO_4$ (anhydrous basis) — 1.0 g.
$MgSO_4.7H_2O$ — 1.0 g.
NaCl — 1.0 g.
$(NH_4)_2SO_4$ — 2.0 g.
$CaCO_3$ — 2.0 g.
Distilled water — 500 ml.
Trace salts solution — 1.0 ml. of solution as in Medium 3.
pH should be between 7.0 and 7.4. Do not adjust if it is within this range.
Mix starch suspension and salts solution.
Add agar (Difco) — 20.0 g.
Liquify agar by steaming at 100° C. for 15–20 minutes.

Medium 4 — Glycerol — asparagine agar:

L-Asparagine (anhydrous basis) — 1.0 g.
Glycerol — 10.0 g.
$K_2HPO_4$ (anhydrous basis) — 1.0 g.
Distilled water — 1.0 liter
Trace salts solution — 1.0 ml. of solution as in medium 3
The pH of this solution is about 7.0 – 7.4.
Do not adjust if it is within this range.
Agar — 200 g.
Liquify agar by steaming at 100° C. for 15–20 minutes.

Medium 5 — Peptone — yeast extract iron agar:

Bacto-Peptone Iron Agar, dehydrate (Difco) — 36.0 g.
Bacto-Yeast Extract (Difco) — 1.0 g.
Distilled water — 1.0 liter
pH should be 7.0–7.2 before autoclaving; adjust if necessary.
Liquify agar by steaming at 100° C. for 15–20 minutes.

Medium 6 — Tyrosine agar:

Glycerol — 15.0 g.
L-Tyrosine (Difco) — 0.5 g.
L-Asparagine (Difco) — 1.0 g.
$K_2HPO_4$ (anhydrous basis) — 0.5 g.
$FeSO_4.7H_2O$ — 0.01 g.
Distilled water — 1.0 liter
Trace salts solution of solution as in medium 3 — 1.0 ml.
Adjust to pH 7.2 – 7.4
Bacto-Agar — 20.0 g.
Liquify by steaming at 100° C. for 15–20 minutes.

The trace salts solution which are used as directed in media 2,3 and 4 are as follows:
$FeSO_4.7H_2O$ — 0.1 g.
$MnCl_2.4H_2O$ — 0.1 g.
$ZnSO_4.7H_2O$ — 0.1 g.
Distilled water — 100.0 ml.

In Table I, spore-mass, color of substrate mycelium (underside), presence of soluble pigment and amount of growth and sporulation are indicated for Mediums 1 to 6. The data in Table I were recorded after 14 days growth of Streptomyces X-11837 at 28° C., color are described according to the Color Harmony Manual, 4th Edition, 1958 (Container Corp. of America).

TABLE 1

Cultural Characteristics of *Streptomyces* sp. X-11837

| Medium | Amount of Growth Degree of Sporulation | Spore Mass Color | Color of Substrate (Underside) Mycelium | Presence of Soluble Pigment |
|---|---|---|---|---|
| 1 | Abundant growth, well sporulated, liquid exudate | 2ih (dark covert gray) in center; 3 ca (pearl pink) toward edge; b (oyster white) at edge | 31 g (adobe brown); 3gc (light tan) at edges; patches of 3nl (dark brown) | — |
| 2 | Moderate growth, moderate to well sporulated | 3li (beaver) in center, a few flecks of c (light gray) at edge | 3ig (beige brown) under sporulated part; 2 gc (bamboo) at edge | — |
| 3 | Poor growth, little sporulation | b (oyster white) where sporulated | between 3 ie (camel) and 3 gc (beige) | — |
| 4 | Moderate growth, moderate sporulation | 3 ig (beige brown) mostly, 2 dc (natural) at edge | 2 fe (covert gray) where sporulated, 2 dc (natural) at edges where not sporulated | — |
| 5 | Moderate growth, moderate sporulation | b (oyster white) in center | | brown |
| 6 | Abundant growth, well sporulated, liquid exudate | 3 ig (beige brown) center, 2 dc (natural) at edge | | diffuse pink on plate, but not concentrated around colonies |

The Streptomyces sp. X-11837 utilized D-glucose, D-fructose, D-galactose, L-arabinose, D-xylose, sucrose, raffinose and D-mannitol, did not grow with L-rhamnose, myo-inositol, salicin or cellulose, hydrolyzed starch and gave a positive gelatinase reaction.

Growth was observed in a liquid medium of (Tryptone Yeast Extract Broth, Difco) at 28° C., 37° C. and 45° C. but was poor at 45° C. after 24 hours. No growth occurred at 50° C. Growth was accompanied by darkening of the medium at 28° C. and 37° C. but at 45° C. no dark pigment was produced. The organism grew on agar plates of Medium 1 and 2 at 28° C. to 37° C. and 45° C.

The culture produced hydrogen sulfide (darkending in Medium 5) but not melanin (no dark color in Medium 6). Growth was observed in liquid medium 7 with sodium chloride concentration up to 7%.

Streptomyces X-11387 when grown under suitable conditions, produces the compound of formula I. A fermentation broth containing Streptomyces X-11837 is prepared by innoculating spores or mycelia of the organism producing the compound of formula I into a suitable medium and then cultivating this medium under aerobic conditions. For the production of a compound of the formula I, cultivation on a solid medium is possible but for production in large quantities, cultivation in the liquid medium is preferable. The temperature of cultivation can vary over a wide range, i.e., from 15° C. to 40° C., within which the organism can grow but a temperature of 26° C. to 30° C. in a substantially neutral pH are preferred. In the submerged aerobic fermentation of the organism for the production of a compound of the formula I, the medium may contain any suitable carbon source. Among the preferred suitable carbon sources are included commercially available glyceride oil or a carbohydrate such as glycerol, glucose, maltose, lactose, dextrin, starch, etc. in pure or cured states. Furthermore, the medium should contain a source of nitrogen. Any conventional nitrogen source can be utilized in the medium in accordance with this invention. Among the preferred nitrogen sources are organic materials such as soybean meal, distillers' solubles, peanut meal, cotton seed meal, meat extract, peptone, fish meal, yeast extract, corn steep liquor, etc. and, when desired, inorganic sources of nitrogen such as nitrites and ammonium salts and mineral salts such as ammonium sulfate, magnesium sulfate and the like. The medium may, if desired, also contain sodium chloride, potassium chloride, potassium phosphate and the like and buffering agents such as sodium citrate, calcium carbonate or phosphates and trace amounts of heavy metal salts. In aerated submerged culturing procedures, an anti-foam agent such as liquid paraffin, fatty oils or silicon compounds is used. More than one kind of carbon source, nitrogen source, or anti-foam source may be used in the production of a compound of the formula I.

In carrying out the fermentation, any conventional method of aerobic fermentation under the conditions of temperature and pH designated above can be utilized. In carrying out the fermentation, the fermentation can be carried out under the submerged aerobic conditions for a period of time of at least when activity against E.coli or Bacillus is imparted to the aqueous solution.

In general, the production of the compound of formula I by submerged aerobic fermentation occurs within six hours. However, if desired, fermentation can be carried out for periods of four days or over. As is the custom, the maximum antibiotic production occurs within seventeen to thirty-five hours. If desired, fermentation periods of greater than four days can be utilized. However, in view of the fact that no additional beneficial results are achieved by utilizing such long fermentation times, these long fermentation times are seldom utilized.

As indicated above, the compound of formula I is prepared under submerged aerobic conditions. Preferably submerged fermentation entails the production of a large quantities of the compound of formula I in accordance with conventional procedures. Small quantities of the compound of formula I are also obtained by shake-flask cultures. As is customary in aerobic submerged culture processes, sterile air is blown through the culture medium. For efficient growth of the organism and production of the compound of the formula I, the volume of air employed in the production is above 0.1 volumes of air per minutes per volume of culture medium. Optimun growth occurs when the volume of air employed is between 0.5 and 1 volumes of air per minute per volume of culture production medium. The production of the compound of formula I can be followed during the fermentation by testing samples of the broth for activity against organisms known to be sensitive to the compound of formula I. The bioassay is conveniently effected by paper disc assay on agar plates.

Following its production under submerged aerobic conditions, the compound of formula I can be recovered from the fermentation broth by methods commonly employed in the fermentation art. Antibiotic activity produced during the fermentation of the compound of the formula I producing organisms occurs in the antibiotic broth. Accordingly, isolation techniques employed in the production of such antibiotics are designed to permit maximum recovery of the compound of formula I from the broth. Thus, for examples, mycelia and undissolved solids are removed from the fermentation broth by conventional means such as filtration and the compound of formula I recovered from the filtered broth by techniques such as ion exchange or absorption.

The compound of formula I having basic amino groups can form salts with acids. The compound of formula I can form salts with acid substances and such salts can be prepared by conventional techniques with such pharmaceutically acceptable acids as hydrochloric acid, hydrobromic acid, sulfuric acid, acetic acid, citric acid and the like. All that is required of the salt is that it provide a pharmaceutically acceptable salt of the compound of formula I.

In accordance with another embodiment of this invention, the compound of formula I is prepared from the compound of formula II. In the first step of this procedure, the compound of formula II is converted to a compound of the formula:

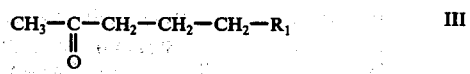

wherein $R_1$ is a leaving group.

In the compound of formula III, $R_1$ can be any conventional leaving group. Among the preferred leaving groups are alkyl sulfonyloxy such as methyl sulfonyloxy, arylsulfonyloxy, such as p-toluenesulfonyloxy, phenyl sulfonyloxy, napthylyl sulfonyloxy, etc. and halides such as chloride or bromide. Any conventional method of converting a hydroxide to a leaving group can be utilized in this procedure of formula II to a compound of formula III.

In the next steps of the procedure of the conversion of a compound of formula II to a compound of formula I, the compound of formula III is converted to 2-methyl arginine (the racemate of the compound of formula I) which has the formula:

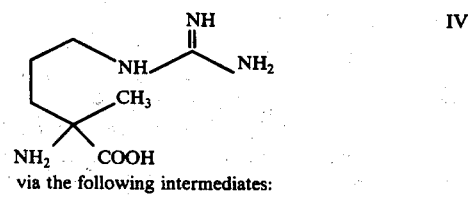

via the following intermediates:

-continued

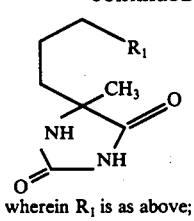  V wherein R₁ is as above;

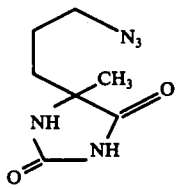  VI

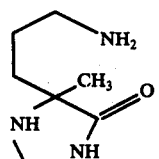  VII

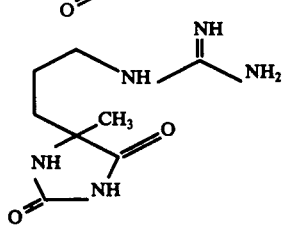  VIII

The compound of formula III is converted to the compound of formula V via a Bucherer-Henze reaction. Any of the conditions conventional in Bucherer-Henze reactions can be utilized to effect this conversion. Generally, this reaction is carried out by treating the compound of formula III with an alkali metal cyanide and ammonium carbonate. Generally this reaction is carried out in the presence of a polar solvent particularly a lower alkanol. In carrying out this reaction, temperatures of from 30° C. to 70° C. are utilized.

In accordance with another embodiment of this reaction, the compound of formula V can be prepared from a compound of the formula:

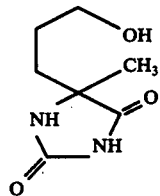  V-B

A compound of formula V can be formed from the compound of formula V-B utilizing any conventional method of converting a hydroxy group to a leaving group.

The compound of formula V is converted to the compound of formula VI by treating the compound of formula V with an alkali metal azide such as sodium azide in a polar solvent. In carrying out this reaction, any conventional polar solvent or mixture of polar solvents can be utilized. Among the preferred polar solvents are water, dimethyl formamide, lower alkanols, etc. The reaction can be carried out at temperatures of from 20° C. to 200° C. Generally, temperatures from about 60°-85° C. are preferred.

The compound of formula VI can be converted to the compound of formula VII by hydrogenolysis. Any conventional method of hydrogenolysis can be utilized to affect this conversion. Among the preferred methods is to treat the compound of formula VI with hydrogen in the presence of a hydrogenation catalyst. Any conventional hydrogenation catalyst can be utilized. Among the preferred hydrogenation catalysts are included platinum oxide, nickel, etc. Generally, this reaction is carried out in a lower alkanol solvent. On the other hand, any conventional inert organic solvent can be utilized to carry out this reaction. In carrying out this reaction, temperature and pressure are not critical and this reaction can be carried out at room temperature. On the other hand, elevated temperatures and/or elevated pressures can be utilized. Generally, it is preferred to carry out this reaction at room temperature.

The compound of formula VII is converted to the compound of formula VIII by treating the compound of formula VII with either a compound of the formula:

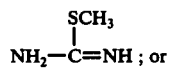  IX-A a compound of the formula, or

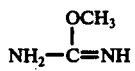  IX-B or a compound of the formula:

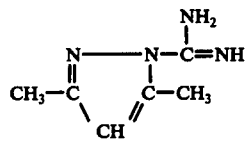  IX-C

This reaction is carried out in an aqueous medium in the presence of an inorganic base. Any conventional inorganic base such as an alkali metal hydroxide or an alkaline earth metal hydroxide can be utilized. In carrying out this reaction, temperature and pressure are not critical and this reaction can be carried out at room temperature and atmospheric pressure. If desired, higher or lower temperatures or pressures can be utilized. Generally this reaction is carried out at a temperature of from 0° C to 100° C. with temperatures of about 20°-50° C. being preferred.

The compound of formula VIII is converted to the compound of formula IV by acid hydrolysis. Any conventional method of acid hydrolysis can be utilized to carry out this reaction. Among the preferred methods of carrying out this reaction is treating the compound of formula VIII with an inorganic mineral acid such as hydrochloric acid, sulfuric acid, etc. in an aqueous medium. In carrying out this reaction, temperatures of about 50°-120° C. are generally utilized.

In order to isolate the compound of the formula IV from the aqueous medium in which it is formed in a crystallazine form, the compound of formula IV is converted to its salt. In this manner, the compound of formula IV in the form of a syrup is converted to a crystalline solid. Any of the conventional salt forms of the compound of the formula IV can be utilized for this purpose. Among the conventional salt forms are included salts with mineral acids such as hydrochloric, hydrobromic and sulfuric, or organic acids such as substituted or unsubstituted benzenesulfonic acids, picric acid, 2-nitroindanedione, etc.

In accordance with another embodiment of the invention, the compound of formula III is converted to the compound of formula IV via the following intermediates:

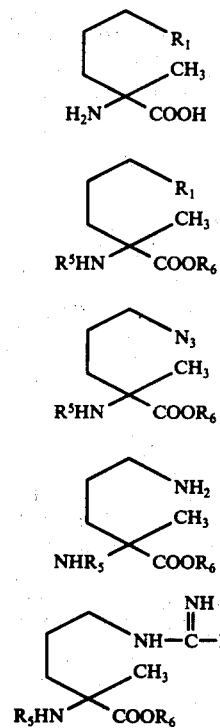

V-A

V-C

VI-A

VII-A

VIII-A wherein $R_1$ is as above; $R_5$ is acyl, aroyl, carbobenzoxy and t-butoxy; and $R_6$ is lower alkyl.

The compound of formula III is converted to the compound of formula V-A by a Strecker reaction. In this reaction, the compound of the formula III is reacted with an alkali metal cyanide such as sodium cyanide, potassium cyanide, etc. in the presence of ammonium hyroxide or an ammonium salt. Any conventional inorganic ammonium salt such as ammonium chloride, ammonium bromide, ammonium carbonate can be utilized. In carrying out this reaction, any of the conditions conventional in the Strecker reaction can be utilized. The compound of the formula V-A is converted to the compound of formula V-C by protecting the free amino group in the compound of the formula V-A with an amide and protecting the free carboxyl group in the compound of the formula V-A as an ester. In forming the amide, the substituent $R_5$ can be any acyl or aroyl group. Among the preferred acyl groups are lower alkanoyl, i.e., lower alkanoyl groups containing from 2 to 7 carbon atoms such as acetyl, propionyl, etc. On the other hand, $R_5$ can be an aroyl group such as benzoyl. In carrying out this reaction, any conventional method of converting an amine to an amide can be utilized. On the other hand, the amine group can be protected by $R_5$ being carbobenzoxy or t-butoxy. Any method of converting an amine group to a carbobenzoxy or t-butoxy amine can be utilized in this conversion.

The compound of formula V-C can be converted to the compound of formula VI-A by treating the compound of formula V-C with an alkali metal azide in accordance with the procedure described in connection with the conversion of a compound of formula V to a compound of formula VI. The azide of formula VI-A can be converted to the amine of formula VII-A by hydrogenolysis in accordance with the method hereinbefore described in connnection with the conversion of a compound of the formula VI to a compound of the formula VII. The compound of formula VII-A can be converted to the compound of VIII-A by means of reacting the compound of the formula VII-A with any one of the compounds of formulae IX-A, IX-B and IX-C. This conversion is carried out in the same manner as described in connection with the conversion of the compound of the formula VII to a compound of the formula VIII.

The compound of formula VIII-A is converted to the compound of formula IV by hydrolysis. The hydrolysis and isolation of the compound of the formula IV in crystalline form can be carried out in the same manner as described in connection with the conversion of the compound of the formula VIII to the compound of formula IV and its isolation as a crystalline solid in its salt form.

The compound of formula IV either in the form of a salt or in the form of a free base is converted to the mixture containing the following compounds:

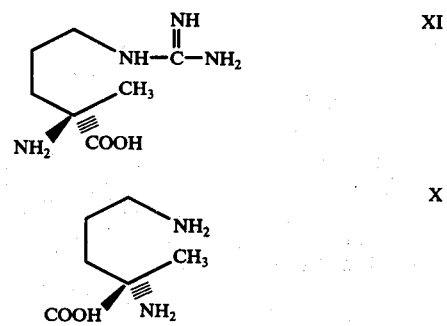

XI

X by enzymatically treating an aqueous solution containing the compound of formula IV with arginase. Any conventional source of arginase can be utilized to provide the arginase in accordance with this reaction. Among the preferred sources of arginase is beef liver. The enzymatic reaction of the compound of formula IV to form the mixture of the compound of formula X and formula XI is carried out in an aqueous medium in the presence of manganese, cobalt or nickel ions. Any conventional source of these ions can be utilized. Among the preferred salts are organic manganese salts such as manganese oleate, manganese maleate and inorganic manganese salts such as manganese carbonate, manganese hydroxide, etc. Generally this enzymatic reation is carried out at a pH of from 7.5 to 11 with a pH of from about 8.5 to 11.0 being preferred. Any conventional method of adjusting an aqueous solution to the aforementioned pH can be utilized. Among the preferred methods is to add a base such as sodium hydroxide, ammonium hydroxide, calcium hydroxide, etc. to the aqueous solution in an amount sufficient to provide the required pH. In carrying out this reaction, temperature and pressure are not critical and this reaction can be carried out at room temperature. On the other hand, higher or lower temperatures can be utilized. Generally, it is preferred to carry out this reaction at a temperature of from 20° C. to 55° C.

In carrying out this reaction, the enzymatic conversion of the compound of the formula IV occurs by treating the compound of formula IV with arginase at a pH of from about 7.5 to 9.5 for a period of at least one day. Generally this reaction is carried out for a period of from one to ten days. However, if desired, reaction times of greater than ten days can be utilized. However, in view of the fact that no additional beneficial results are achieved from utilizing such long reaction times, i.e., over ten days, these reaction times are seldom utilized.

The compound of formulae X and XI can be separated by any conventional means. Among the conventional methods of separating the compounds of formulae X and XI are by chromatography on an ion exchange resin. Any conventional method of ion exchange chromatography can be utilized to affect this separation.

In converting the compound of formula X to the compound of formula I, the compound of formula X is first reacted with a copper (II) salt to form a copper chelate thereof. This reaction takes place in an aqueous medium. Any conventional copper (II) salt which is soluble in water can be utilized to form the copper chelate. Among the preferred copper salts are copper (II) sulfate, copper (II) chloride and copper.(II) carbonate. In carrying out this reaction, temperature and pressure are not critical and this reaction can be carried out at room temperature and atmospheric pressure. On the other hand, elevated and reduced temperatures can be utilized. Generally, it is preferred to carry out this reaction at a temperature of from about 35° C. to 55° C.

The compound of formula I is formed from the copper chelate of formulae X by reacting the copper chelate of the compound of formula X with a compound of the formula IX-A, IX-B or IX-C. This reaction is carried out in the same manner as described in reacting the compound of formula VII with a compound of formula IX-A, IX-B and IX-C to form a compound of the formula VIII. After the reaction of the copper chelate of the compound of formula X with a compound of the formula IX-A, IX-B, IX-C, the copper ions are precipitated as copper sulfide, thus liberating the compound of the formula I.

As used throughout this application, the term "lower alkyl" comprehends both straight and branched chain saturated hydrocarbon groups containing from 1 to 7 carbons atoms such as methyl, ethyl, propyl, isopropyl, etc. As used throughout this application, the term "halogen" includes all four halogens such as bromine, chlorine, fluorine, and iodine. The term "alkali metal" includes sodium potassium, lithium, etc. The term "alkaline earth metal" includes all of the alkaline earth metals such as barium, calcium and magnesium.

As used herein, the term "aryl" designates mononuclear aromatic hydrocarbon groups such as phenyl, tolyl, etc. which can be unsubstituted or substituted in one or more positions with a halogen, nitrile or lower alkyl substituent and polynuclear aryl groups such as naphthyl, anthryl, phenanthryl, azulyl, etc. which can be unsubstituted or substituted with one or more of the aforementioned groups. The preferred aryl groups are the substituted and unsubstituted mononuclear aryl groups, particularly phenyl and tolyl.

The following Examples are illustrative but not limitative of the invention. All temperatures are in degrees Centigrade (° C.) and the ether utilized is diethyl ether. In the Examples, the solvent systems are as follows:

Solvent System A = a mixture of chloroform, methanol and 27% by weight aqueous ammonium hydroxide; 2:2:1 parts by volume;

Solvent System B = a mixture of chloroform, methanol, 27% by weight aqueous ammonium hydroxide and water; 2:4:2:1 parts by volume;

Solvent System C = a mixture of ethanol, water and 27% by weight aqueous ammonium hydroxide; 4:1:1 parts by volume;

Solvent System D = a mixture of 1-butanol, acetic acid, water, 4:1:1 parts by volume; and Solvent System E = a mixture of chloroform and 2-propanol, 9:1 parts by volume.

EXAMPLE 1

Streptomyces sp. X-11837 was maintained on tomato-soy agar slants composed of (g/liter) tomato past, 20; glucose (Cerelose, Corn Products), 10; defatted soybean flour (Soyalose, Central Soya), 10; $CaCO_3$, 2; Bacto-peptone (Difco), 1; $K_2HPO_4$, 1; and agar, 20. Portions of slant growth were added to 6-liter Erlenmeyer flasks containing 2-liters of inoculum medium composed of (g/liter): tomato pomace (Seaboard Supply), 5; dried distiller's solubles (Soludri, Schenley), 5; cottonseed flour (Proflo, Trader's), 5; protopeptone 366 (Wilson), 5; cornstarch (Anheuser Busch), 10; $CaCO_3$, 1; and $K_2HPO_4$, 1. The flasks were incubated at 28° C. for 72 hours on a roatary shaker (250 rpm, 5.08 cm throw). Four liters of the resulting inoculum were added to 225 liters of fermentation medium composed of (g/liter) glucose (Cerelose, Corn Products), 10; Bacto-peptone (Difco), 5; yeast extract (Difco), 3; and $FeSO_4.(NH_4)_2SO_4(NH_4)_2SO_4.6H_2O$, 0.03. The culture was incubated at 28° C. in a 380 liter fermentor, aerated at 0.15 $m^3$/min and agitated at 280 rpm. Silicone antifoam was added as needed to control frothing. After 24 hours the fermentation broth was clarified by centrifugation through infusorial earth.

The clarified broth was passed through a column of 20.5 cm diameter containing 50 liters of sulfonated polystyrene ion exchange resin and the column washed consecutively with 200 liters of water, 200 liters of 5% by volume aqueous pyridine and 50 liters of water. The active fracton was then eluted with 1 N ammonium hydroxide solution and was mostly contained in the first 300 liters of ammoniacal effluent which, upon concentration and freeze-drying, gave crude 2-methyl-L-arganine (55 g., approximately 1% purity).

To achieve additional purification the crude was dissolved in water, the pH of the solution adjusted to 3.5 with diluted hydrochloric acid, filtered and chromatographed on a column of sulfonated polystyrene ion exchange resin (200-14 400 mesh, 68 × 650 mm). The column was developed with a buffer (8 liters) prepared by adding a 0.1 M citric-acid solution to a 0.2 M aqueous dibasic sodium phosphate solution to pH 6.1. Development was continued with 32 liter of the same buffer but containing 5.84 g. of sodium chloride per liter. The antimetabolite was eluted by the sodium-chloride containing buffer and started to emerge in the effluent after 17 liters had passed through the column.

The antimetabolite-containing effluent was desalted by passage through a column containing sulfonated polystyrene ion exchange resin, 50–100 mesh (2.5 liters) followed by a water wash and elution with 1 N aqueous ammonium hydroxide. The biologically active fractions were brought to dryness to yield crude 2-methyl-L-arganine (2.6 g., approximately 20% purity).

This preparation was chromatographed on a column (25 × 280 mm) of silica gel (0.05 – 0.2 mm) prepared by slurrying in chloroform and developed with solvent system B. Most impurities preceded the biologically active fractions, the latter were concentrated to dryness under reduced pressure to yield an amorphous preparation (0.7 g.) containing 2-methyl-L-arginine and arginine in an approximate ratio of 2:1.

Pure 2-methyl-L-arganine was isolated by chromatography of the arginine-containing preparation (200 mg) on a cellulose column, 40 × 215 mm with solvent system A. 2-Methylarginine was eluted first and was quantitatively separated from arginine; concentration of the appropriate fractions gave 2-methyl-L-arganine (133 mg) as amorphous powder.

EXAMPLE 2

5-(3-Chloropropyl)-5-methyl-2,4-imidazolidinedione

To a stirred solution of 5-chloro-2-pentanone (87 g., 0.72 mol) in ethanol (750 ml.) contained in a 3-liter round-bottom flask, equipped with reflux condenser and mechanical stirrer was added a solution of ammonium carbonate (214 g.) in water (525 ml) followed by a solution of potassium cyanide (50 g.) in water (265 ml.). The mixture was stirred at 50–55° C. for 2.5 hours, cooled to 5–10° C. and excess carbonate and cyanide was removed by the slow addition of 6 N aqueous hydrochloric acid (approx. 650 ml.) to pH 4 under stirring. The resulting mixture was concentrated to a volume of approximately 1 liter and refrigerated overnight. The crystalline deposit of 5-(3-chloropropyl)-5-methyl-2,4-imidazolidinedione was filtered off, dried and recrystallized from chloroform/petroleum ether (25.1 g., 0.13 mol, 18%) m.p. 119–121° C.

EXAMPLE 3

5-methyl-5-{3-[(4-methylphenyl)sulfonyloxy]-propyl}-2,4-imidazolinedione

P-toluenesulfonyl chloride (22.5 g., 0.118 mol) was added to a stirred solution of 5-(3-hydroxypropyl)-5-methyl-2,4-imidazolidine-dione (20.0 g, 0.116 mol) in pyridine (250 ml.) at 5° C. The mixture was stirred for one hour, refrigerated overnight and diluted with water (275 ml.) The resulting solution was extracted three times with chloroform (375, 190 and 190 ml.), the combined extracts were washed with 5 N aqueous sulfuric acid (4 × 125 ml.), water (2 × 150 ml.) and saturated aqueous sodium bicarbonate solution (2 × 125 ml). Concentration of the dried chloroform phase yielded 5-methyl-5- {3-[(4-methylphenyl)sulfonyloxy]-propyl}-2,4-imidazolinedione (22.2 g., 0.068 mol, 58%) upon addition of ether and petroleum ether, m.p. 126–127° C.

EXAMPLE 4

5-(3-azidopropyl)-5-methyl-2,4-imidazolidinedione

A solution of sodium azide (13 g, 0.2 mol) in water (100 ml) was added to a solution of 5-(3-chloropropyl)-5-methyl-2,4-imidazolidinedione (19.06 g, 0.1 mol) in dimethylformamide (900 ml.) and the mixture was kept at 75° C. for 21 hours. Iodometric determinations of azide ions indicated the consumption of the expected quantities of azide at that time. The mixture was concentrated to a syrup which was redissolved in chloroform (200 ml.), filtered, diluted with chloroform (500 ml.) and water (100 ml.), the chloroform phase was collected after equilibration and combined with four additional chloroform extracts which were dried (MgSO$_4$) and concentrated. Crystalline 5-(3-azidopropyl)-5-methyl-2,4-imidazolidinedione was obtained from chloroform/petroleum ether (17.3 g, 88%), m.p. 104° C. after one recrystallization from the same solvent.

EXAMPLE 5

5-(3-aminopropyl)-5-methyl-2,4-imidazolidinedione hemisulfate

A suspension of platinum (200 mg) in 2-propanol (50 ml.) and 1 N sulfuric acid (20 ml.) was briefly hydrogenated (3.4 atm) and 5-(3-azidopropyl)-5-methyl-2,4-imidazolidinedione (3.94 g., 0.020 mol) was added. Hydrogenation was continued for 7 hours at 3.4 atmospheres. The catalyst was removed by filtration and the filtrate concentrated to a small volume, addition of 2-propanol afforded 5-(3-aminopropyl)-5-methyl-2,4-imidazolidine dione hemisulfate as prisms, 4.40 g. (0.019 mol, 96%); m.p. 183°–185° C. after one crystallization from aqueous 2-propanol.

EXAMPLE 6

5-(3-[(aminoiminomethyl)amino]propyl)-5-methyl-2,4-imidazolidinedione

The compound 5-(3-aminopropyl)-5-methyl-2,4-imidazolidinedione hemisulfate (229 mg, 1 mmol) was dissolved in 0.418 N aqueous barium hydroxide (3.5 ml.) and S-methylisothiourea (153.1 mg, 1.1 mol) was added. The suspension was shaken at room temperature for 6¼ hours and 0.418 N aqueous barium hydroxide (1 ml.) was added, followed by another 0.5 ml. of the aforementioned barium hydroxide solution 18 hours later. After 4 hours, S-methylisothiourea (70 mg., 0.5 mmol) was added and shaking of the suspension was continued for 66 hours. At that time only traces of 5-(3-aminopropyl)-5-methyl-2,4-imidazolidinedione hemisulfate could be detected. Barium sulfate was filtered off and washed with water, filtrate and washings were applied to a column containing 5 ml. of sulfonated polystyrene ion exchange resin, the column was washed consecutively with water (50 ml.) 10% by volume aqueous pyridine (25 ml.) and 2.5 M aqueous ammonium hydroxide solution (25 ml). Concentration of the ammoniacal effluent gave a colorless syrup from which crystalline 5-(3-[(aminoiminomethyl) amino]propyl)-5-methyl-2,4-imidazolidinedione was deposited on standing (207 mg., 0.97 mmol, 97%). Recrystallization from water afforded 5-(3-[(amino-iminomethyl)amino]propyl)-5-methyl-2,4-imidazolidienedione as fine needles, m.p. 294°–295° C.

EXAMPLE 7

2-Methyl-D,L-arginine

A solution of 5-(3-[(aminoiminomethyl)amino]propyl-5-methyl-2,4-imidazolidinedione (1.39 g, 6.52 mmol) in 6 N hydrochloric acid (14 ml), contained in a sealed glass-tube was heated at 125° C. for 24 hours. The hydrolyzate was evaporated to dryness, redissolved in water and applied to a column (15 × 245 mm) containing sulfonated polystyrene ion exchange resin, 100–200 mesh. The column was washed with water until the effluent was neutral and eluted with 1 N aqueous ammonium hydroxide. Some impurities preceded those fractions containing ninhydrin- and Sakaguchi-positive solutes, latter were combined, concentrated, filtered and taken to dryness to yield 2-methyl-D,L-arginine as amorphous, hydroscopic powder (1.37 g.). This material was dissolved in water (10 ml.) and a 1 M methanolic solution of 2-nitroindanedione was added until a pH of 5.1 was reached. The crystal suspension was concentrated to a small volume and cooled to 0° C. for several hours prior to filtration. The resulting 2-methyl-D,L-arginine 2-nitroindanedione salt dihydrate (2.60 g, 6.26 mmol, 96%) was recrystallized from hot water to give yellow prisms, m.p. 168°-170° C. (dec).

Similarly, amorphous 2-methyl-D,L-arginine base was converted to the hydrochloride by pH-adjustment to 5.1 with 1 M hydrochloric acid. Although crystalline 2-Methyl-DL-arginine hydrochloride could be obtained by the addition of 2-propanol to the methanolic solution of 2-methyl-D,L-arginine hydrochloride, the yields of crystalline product were only 30%, m.p. 243°-246° C.

EXAMPLE 8

2-methyl-D-arginine and 2-methyl-L-ornithine

A solution of 2-methyl-D,L-arginine 2-nitroindanedione salt dihydrate (1.02 g., 2.46 mmol) in water (100 ml.) was charged to a 15 ml. column of sulfonated polystyrene ion exchange resin (50–100 mesh). 2-Nitroindanedione was eluted with water and 2-methyl-D,L-arginine with 5 N aqueous ammonium hydroxide solution. Concentration of the ammoniaca effluent gave a colorless residue (550 mg) which was dissolved in water (15 ml.) adjusted to pH 9.5 (HCl) and digested at 37° C. under stirring for 4 days with a preincubated (37°, 4 hour) solution prepared by dissolving arginase (10 mg) in 20 ml. of 0.05 M aqueous manganese maleate buffer (prepared by dissolving 845 mg. MnSO$_4$ in 30 ml. water; dissolving 580.4 mg. maleic acid in 50 ml. of water and then adjusting to a pH of 8.1 with NaOH. The solutions were combined and the final volume was adjusted to 100 ml. with water). The resulting solution was stirred for 10 minutes with charcoal (200 mg.) before filtering and the filtrate was applied to a column of sulfonated polystyrene ion exchange resin (200400 mesh, 10 × 310 mm). Washing the column with water removed maleic and sulfuric acid and subsequent development with 1 N aqueous ammonium hydroxide solution first eluted 2-methyl-L-ornithine followed by 2-methyl-D-arginine as determined by tlc. The appropriate fractions were pooled, concentrated to dryness to yield 2-methyl-L-ornithine, 227 mg. and 2-methyl-D-arginine as colorless syrups.

An aqueous solution of 2-methyl-L-ornithine was adjusted to pH 5 with hydrochloric acid, concentrated and diluted with ethanol to yield 2-methyl-L-ornithine hydrochloride as prisms, 165 mg. (0.90 mmol, 73%) m.p. 222°-224° C.

EXAMPLE 9

2-methyl-L-arginine

A solution of 2-methyl-L-ornithine hydrochloride (143 mg., 0.78 mmol) in water (2 ml.) was heated on the steam bath for 5 minutes with basic cupric carbonate and filtered to form the copper II complex of 2-methyl-L-ornithine as the filtrate. Filtrate and washings were cooled to 5° C, mixed with O-methylisourea hydrogen sulfate (148 mg, 0.86 mmol) and 1.0 N aqueous sodium hydroxide solution (1.72 ml) and allowed to stand at room temperature for 6 days. The solution was acidified to pH 1.8 with 2 N aqueous hydrochloric acid, saturated with hydrogen sulfide and filtered through charcoal. Filtrate and washings were applied to a column of sulfonated polystyrene ion exchange resin (220–400 mesh, 12.7 × 240 mm) which was washed with water (150 ml.) and developed with 1 N aqueous ammonium hydroxide solution eluting unreacted 2-methyl-L-ornithine followed by pure 2-methyl-L-arginine as indicated by the systems A ~ D and isolated as 2-nitroindanedione salt as previously described (80 mg., 0.19 mmol).

We claim:

1. A process for producing a compound of the formula:

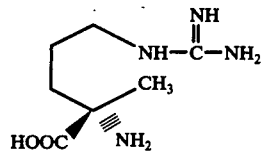

which comprises cultivating a strain of Streptomyces X-11837 in an aqueous carbohydrate solution containing a nitrogenous nutrient under submerged aerobic conditions until activity versus Escherichia Coli B is imparted to said solution and then recovering said compound from said solution.

2. The process of claim 1 wherein the aqueous solution is cultured at a temperature of from 15° C. to 40° C.

* * * * *